US011077740B2

(12) United States Patent
Mejia et al.

(10) Patent No.: US 11,077,740 B2
(45) Date of Patent: Aug. 3, 2021

(54) FORCED AIR SYSTEM OUTLET FOR A VEHICLE WITH A LOADABLE TRAY TO HOLD AN AROMATIC AGENT

(71) Applicant: Ford Global Technologies, LLC, Dearborn, MI (US)

(72) Inventors: Federico Emilio Mejia, Huixquilucan (MX); Cecilia Abigail Ayala Rubio, Mexico City (MX); Carlos Pietra Santa, Naucalpan (MX); Jose Sandoval, Cuautitlan Izcalli (MX); Mario Hernandez, Cuautitlan Izcalli (MX)

(73) Assignee: Ford Global Technologies, LLC, Dearborn, MI (US)

( * ) Notice: Subject to any disclaimer, the term of this patent is extended or adjusted under 35 U.S.C. 154(b) by 247 days.

(21) Appl. No.: 16/270,146

(22) Filed: Feb. 7, 2019

(65) Prior Publication Data

US 2020/0254853 A1    Aug. 13, 2020

(51) Int. Cl.
*B60H 3/00* (2006.01)
*A61L 9/12* (2006.01)

(52) U.S. Cl.
CPC .............. *B60H 3/0028* (2013.01); *A61L 9/12* (2013.01); *B60H 2003/0057* (2013.01)

(58) Field of Classification Search
CPC .. B60H 3/0007; B60H 3/0014; B60H 3/0021; B60H 3/0028; B60H 2003/0057; B60H 3/0035; A61L 9/12
USPC ...................... 49/155; 206/91, 110, 267, 758; 222/142.8; 239/58–59; 454/141–142, 454/237–253, 152–156, 265–268, 454/277–283, 309–320
See application file for complete search history.

(56) References Cited

U.S. PATENT DOCUMENTS

| 4,722,264 | A | * | 2/1988 | DeGuisseppe | ....... B60H 3/0007 |
| | | | | | 261/60 |
| 5,141,707 | A | * | 8/1992 | Brite | ......................... A61L 9/12 |
| | | | | | 422/124 |
| 5,269,723 | A | | 12/1993 | Bender | |
| 2002/0139251 | A1 | | 10/2002 | Simmons | |

(Continued)

FOREIGN PATENT DOCUMENTS

DE          10044894 A1    3/2002
EP          0684151 A1 *  11/1995  ........... B60H 3/0021

(Continued)

*Primary Examiner* — Edelmira Bosques
*Assistant Examiner* — Benjamin Trettel
(74) *Attorney, Agent, or Firm* — David Coppiellie; Price Heneveld LLP

(57) ABSTRACT

An outlet for a forced air system of a vehicle comprising: a primary air flow chamber; a secondary air flow chamber adjacent the primary air flow chamber; an air flow diverter between the primary air flow chamber and the secondary air flow chamber that diverts a portion of air flow from the primary air flow chamber and into the secondary air flow chamber, with the diverted portion of the air flow flowing back into the primary air flow chamber; and a tray configured to retain an aromatic agent, the tray movable into and out of the secondary air flow chamber to selectively place the aromatic agent in contact with air flowing through the secondary air flow chamber to aromatize the air before flowing back into the primary air flow chamber.

20 Claims, 17 Drawing Sheets

(56) References Cited

U.S. PATENT DOCUMENTS

2006/0005711 A1      1/2006  Olefson
2007/0178821 A1 *    8/2007  Zimmerman ........ B60H 3/0021
                                                   454/69
2017/0129313 A1      5/2017  Avendano Arenas et al.

FOREIGN PATENT DOCUMENTS

FR         2833532 A1 *   6/2003   ............... A61L 9/12
FR         2841184 A1 *  12/2003   ........... B60H 3/0007
KR        101596405 B1    2/2016
WO       2013111842 A1    8/2013

* cited by examiner

FORCED AIR SYSTEM OUTLET FOR A VEHICLE WITH A LOADABLE TRAY TO HOLD AN AROMATIC AGENT

FIELD OF THE INVENTION

The present invention generally relates to an outlet for a forced air system of a vehicle, and more particularly, to an outlet that includes a tray that can be loaded with an aromatic agent to aromatize air flowing through the outlet and into an interior of the vehicle.

BACKGROUND OF THE INVENTION

Sometimes the air flowing through the interior of the vehicle is malodorous. Vehicles sometimes employ ways to mask the malodorous odors, but those ways either have poor aesthetics or are too expensive to implement in many vehicles.

SUMMARY OF THE INVENTION

According to a first aspect of the present invention, an outlet for a forced air system of a vehicle comprises: a primary air flow chamber defining a primary air flow path from an entrance to an exit; a secondary air flow chamber; a dividing wall separating the secondary air flow chamber from the primary air flow chamber, the dividing wall having apertures to allow a portion of the air in the primary air flow path to flow in a secondary air flow path in sequence from the primary air flow chamber, into the secondary air flow chamber, and back into the primary air flow chamber; and a tray cooperating with the secondary air flow chamber, the tray including a reservoir to hold an aromatic agent, and the tray manipulable to, from, and between a full insertion position where the reservoir is entirely disposed in the secondary air flow chamber and a loading position where the reservoir is entirely extracted the secondary air flow chamber.

Embodiments of the first aspect of the invention can include any one or a combination of the following features:
  the primary air flow chamber includes opposing side walls and a wall that opposes the dividing wall;
  the secondary air flow chamber includes at least one side wall and a wall that opposes the dividing wall;
  the apertures of the dividing wall include an entrance aperture and an exit aperture, the entrance aperture being disposed closer to the entrance of the primary air flow chamber than the exit aperture;
  the dividing wall further includes at least one air flow diverter projecting into the primary air flow chamber toward the wall of the primary air flow chamber that opposes the dividing wall, the air flow diverter having a first portion that includes the entrance aperture and a second portion that includes the exit aperture, the air flow diverter projecting into the primary air flow chamber to the greatest extent at the first portion;
  the air flow diverter includes a first edge defining the entrance aperture, the first edge being at least approximately orthogonal relative to the primary air flow path;
  the first edge being at least approximately orthogonal to the opposing side walls of the primary air flow chamber;
  the air flow diverter includes a surface extending from the entrance aperture to the exit aperture and facing the tray when the tray is in the full insertion position, the surface sloping closer to the tray from the entrance aperture to a closest point, where a distance between the tray and the surface is at a minimum, and then sloping away from the tray from the closest point to the exit aperture;
  the tray includes a primary reservoir surface and one or more side surfaces extending orthogonally from the primary reservoir surface to define the reservoir;
  the primary reservoir surface is at least approximately parallel to the wall of the secondary air flow chamber that opposes the dividing wall;
  the tray further includes a pull tab that extends away from the reservoir and is accessible externally from the outlet when the tray is in the full insertion position; and
  a regulator cooperating with the apertures of the dividing wall to regulate a volume of air able to flow in the secondary air flow path, the regulator manipulable to, from, and between a full open position where the regulator does not prevent air from flowing in the secondary air flow path and a full closed position where the regulator prevents air from flowing in the secondary air flow path, the regulator further including a tab that is accessible externally from the outlet to allow for selective manipulation of the regulator to, from, and between the full open position and the full closed position.

According to a second aspect of the present invention, a vehicle comprises: an interior; a forced air system to force air to flow into the interior; and an outlet through which air that the forced air system forces flows before flowing into the interior, the outlet comprising: a primary air flow chamber defining a primary air flow path from an entrance to an exit, the exit being closer to the interior than the entrance; a secondary air flow chamber; a dividing wall separating the secondary air flow chamber from the primary air flow chamber, the dividing wall having apertures to allow a portion of the air in the primary air flow path to flow in a secondary air flow path in sequence from the primary air flow chamber, into the secondary air flow chamber, and back into the primary air flow chamber; and a tray cooperating with the secondary air flow chamber, the tray including a reservoir to hold an aromatic agent, and the tray manipulable to, from, and between a full insertion position where the reservoir is entirely disposed in the secondary air flow chamber and a loading position where the reservoir is disposed sufficiently into the interior to allow for the insertion of an aromatic agent into the reservoir.

Embodiments of the second aspect of the invention can include any one or a combination of the following features:
  the primary air flow chamber includes opposing side walls and a wall that opposes the dividing wall;
  the secondary air flow chamber includes at least one side wall and a wall that opposes the dividing wall;
  the apertures of the dividing wall including an entrance aperture and an exit aperture, the exit aperture being disposed closer to the interior of the vehicle than the entrance aperture;
  the dividing wall further includes at least one air flow diverter projecting into the primary air flow chamber, the air flow diverter having a first portion that includes the entrance aperture and a second portion that includes the exit aperture, the air flow diverter projecting into the primary air flow chamber to the greatest extent at the first portion;
  the air flow diverter includes a first edge defining the entrance aperture, the first edge being at least approximately orthogonal to the primary air flow path;

the air flow diverter includes a surface extending from the entrance aperture to the exit aperture and facing the tray when the tray is in the full insertion position, the surface sloping closer to the tray from the entrance aperture to a closest point;

the tray includes a primary reservoir surface and one or more side surfaces extending orthogonally from the primary reservoir surface to define the reservoir;

the tray further includes a pull tab that extends into the interior, and is available for manipulation, when the tray is in the full insertion position;

the outlet further comprises a regulator cooperating with the apertures of the dividing wall to regulate a volume of the air to flow in the secondary air flow path, the regulator manipulable to, from, and between a full open position where the regulator does not prevent air from flowing in the secondary air flow path and a full closed position where the regulator prevents air from flowing in the secondary air flow path, the regulator further including a tab that is accessible from the interior to allow for selective manipulation of the regulator to, from, and between the full open position and the full closed position;

a center console, and the outlet is disposed at the center console;

the tray includes a primary reservoir surface and one or more side surfaces extending orthogonally from the primary reservoir surface to define the reservoir;

the tray further includes a pull tab that extends into the interior, and is available for manipulation, when the tray is in the full insertion position;

the secondary air flow chamber has a forward wall with an inlet through which the tray extends and can move, the forward wall having an interior facing surface; and the tray has an interior facing surface, from which the pull tab extends, the interior facing surface of the tray being at least approximately flush with the interior facing surface of the inlet.

According to a third aspect of the present invention, an outlet for a forced air system of a vehicle comprises: a primary air flow chamber; a secondary air flow chamber adjacent the primary air flow chamber; an air flow diverter between the primary air flow chamber and the secondary air flow chamber that diverts a portion of air flow from the primary air flow chamber and into the secondary air flow chamber, with the diverted portion of the air flow flowing back into the primary air flow chamber; and a tray configured to retain an aromatic agent, the tray movable into and out of the secondary air flow chamber to selectively place the aromatic agent in contact with air flowing through the secondary air flow chamber to aromatize the air before flowing back into the primary air flow chamber.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 3:
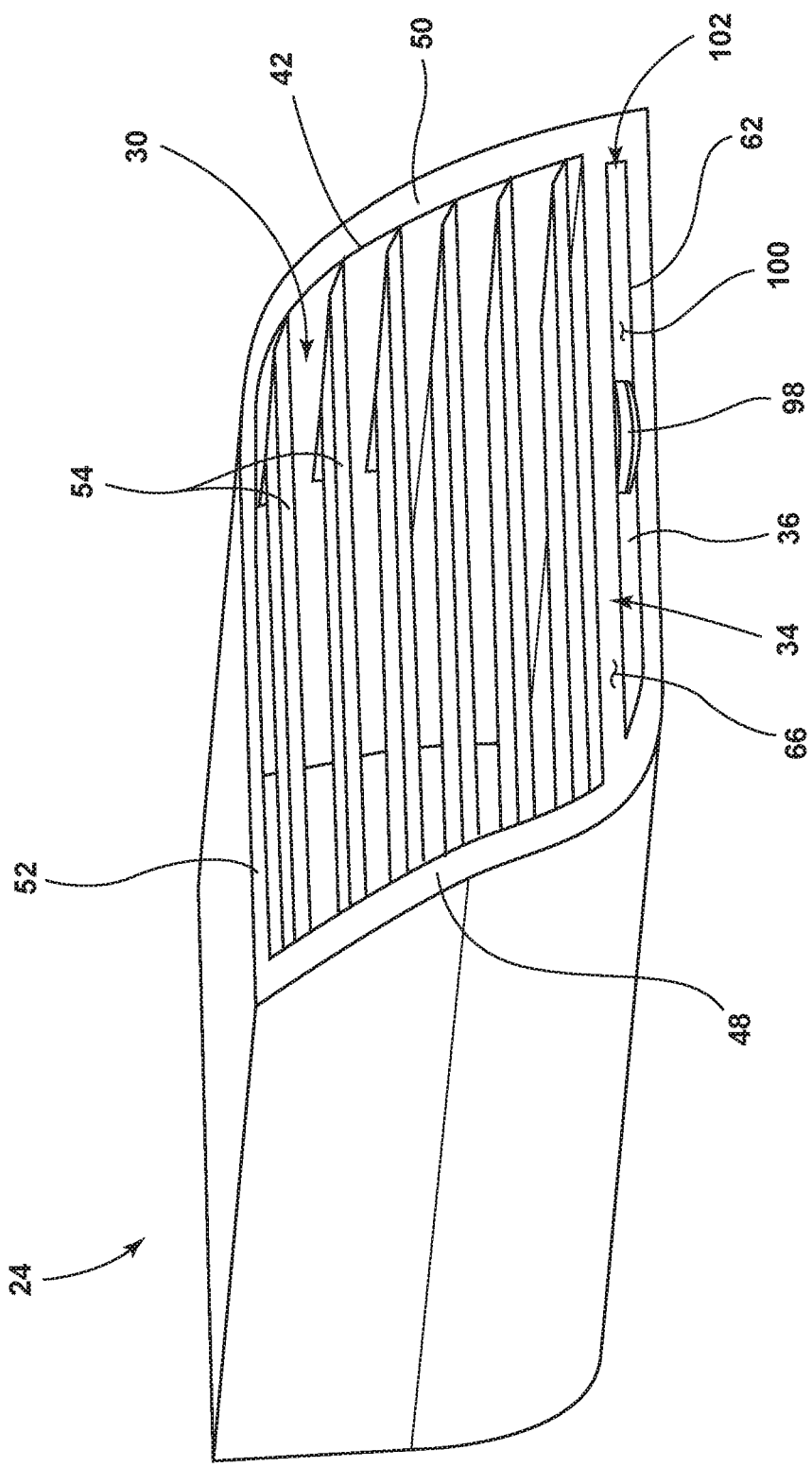
FIG. 3 is a perspective view of the outlet of FIG. 1, illustrating various walls forming a primary air flow chamber with slats near an exit of the primary air flow chamber and a tray positioned at a full insertion position within the outlet below the primary air flow chamber.
Figure 4:
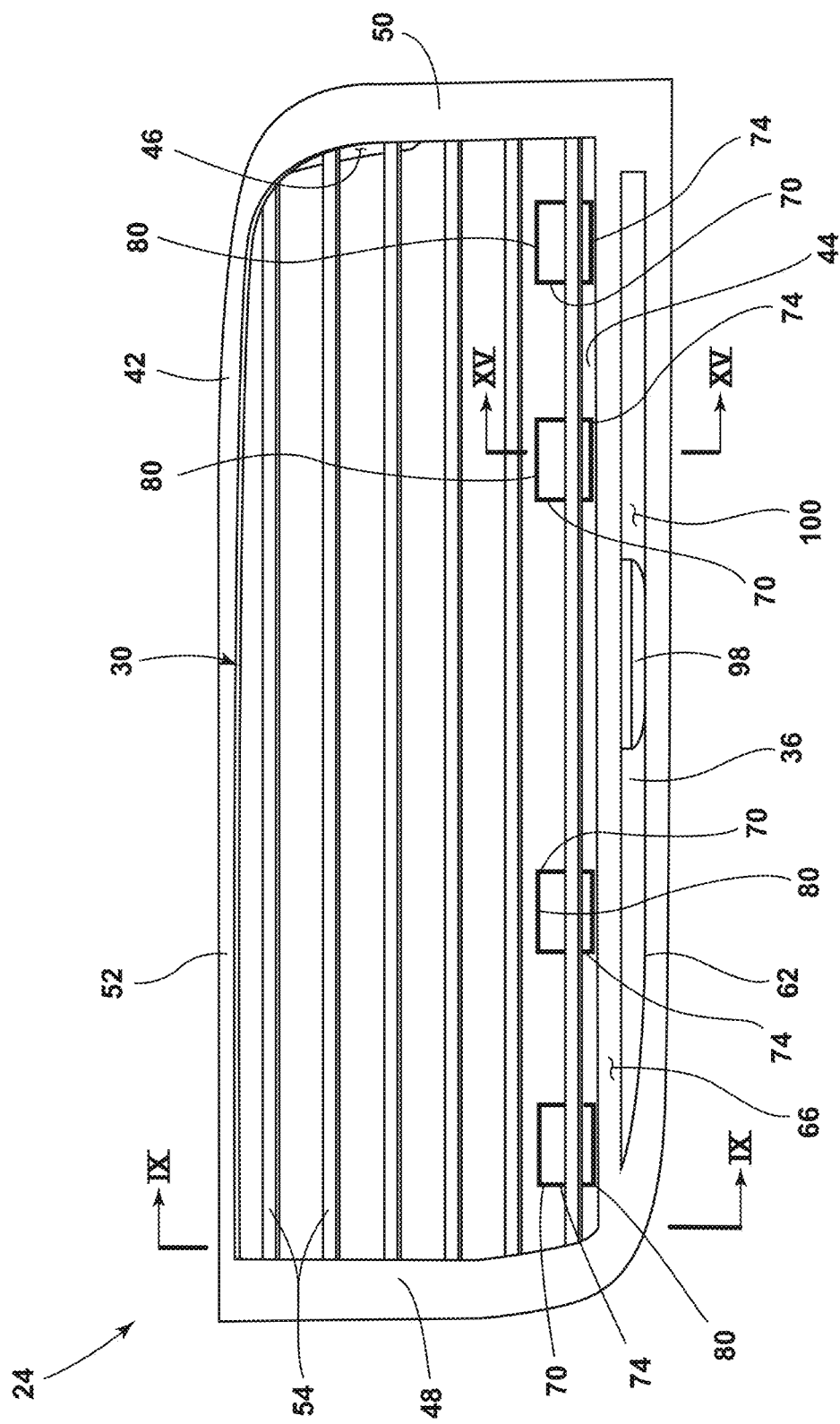
FIG. 4 is a front view of the outlet of FIG. 1, illustrating several air flow diverters projecting into the primary air flow chamber and including exit apertures.
Figure 5:
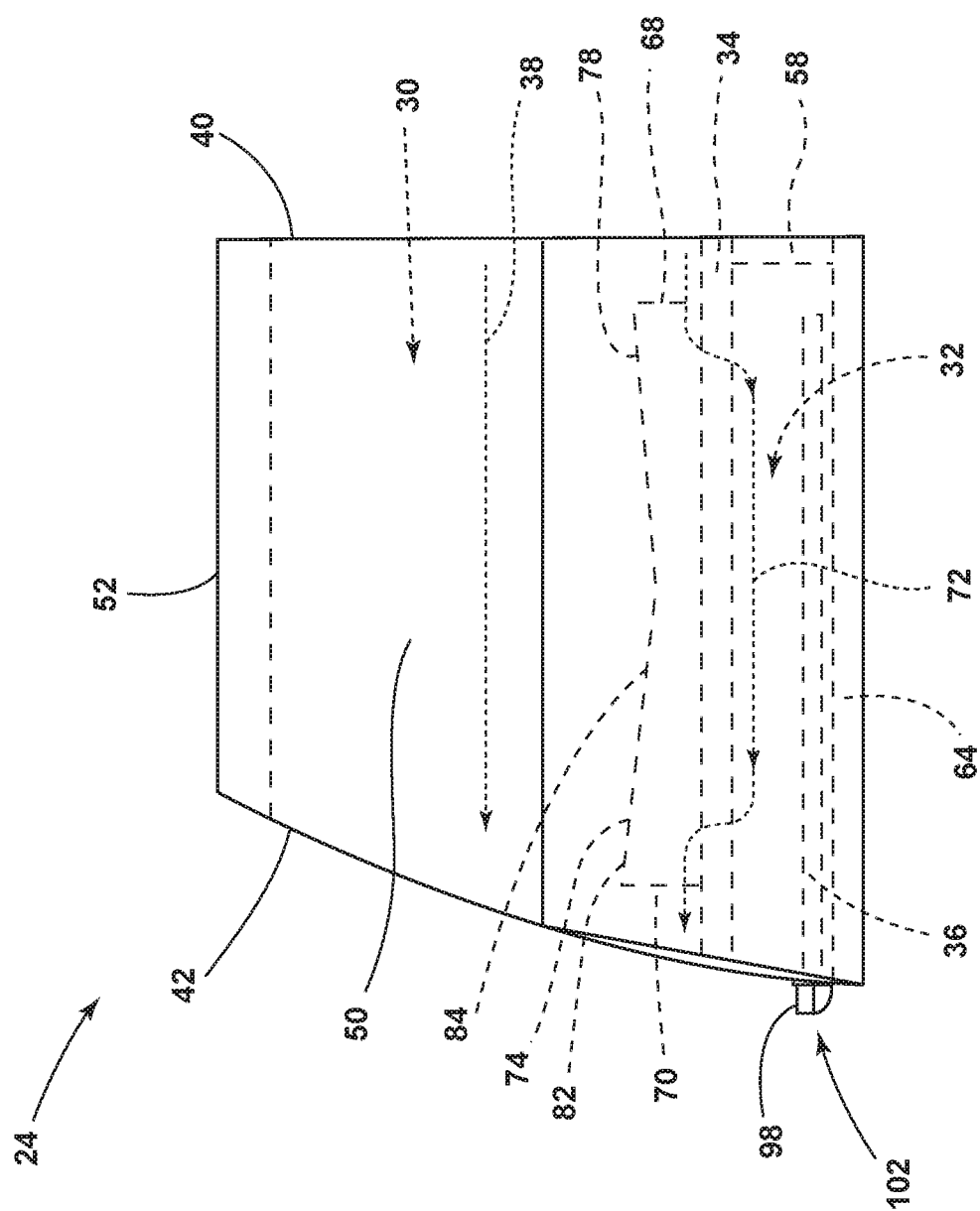
FIG. 5 is a side view of the outlet of FIG. 1, illustrating a secondary air flow chamber in phantom below a dividing wall separating the secondary air flow chamber from the primary air flow chamber.
Figure 6:
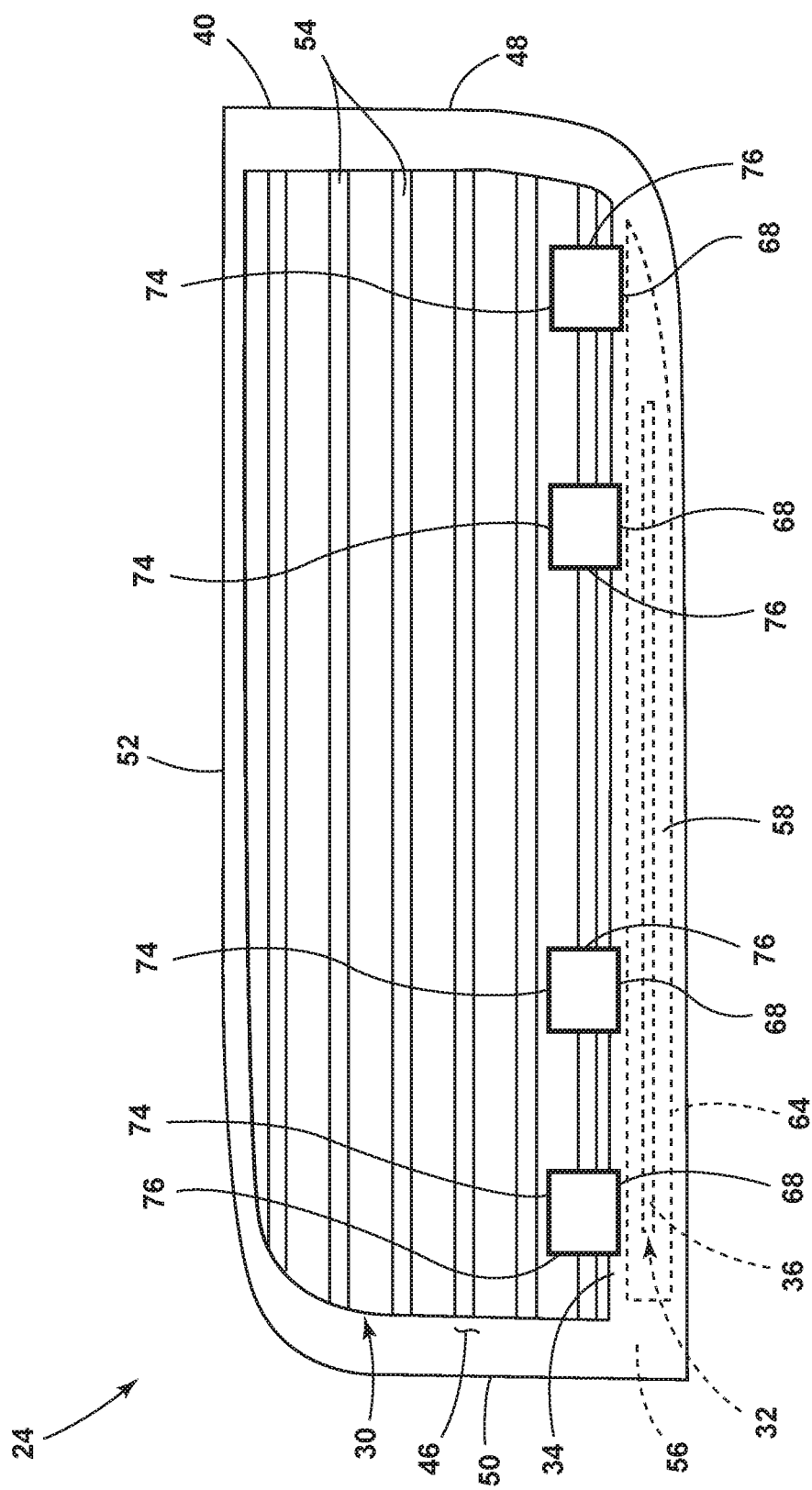
FIG. 6 is a rear view of the outlet of FIG. 1, illustrating the air flow diverters having entrance apertures into the secondary air flow chamber.
Figure 7:
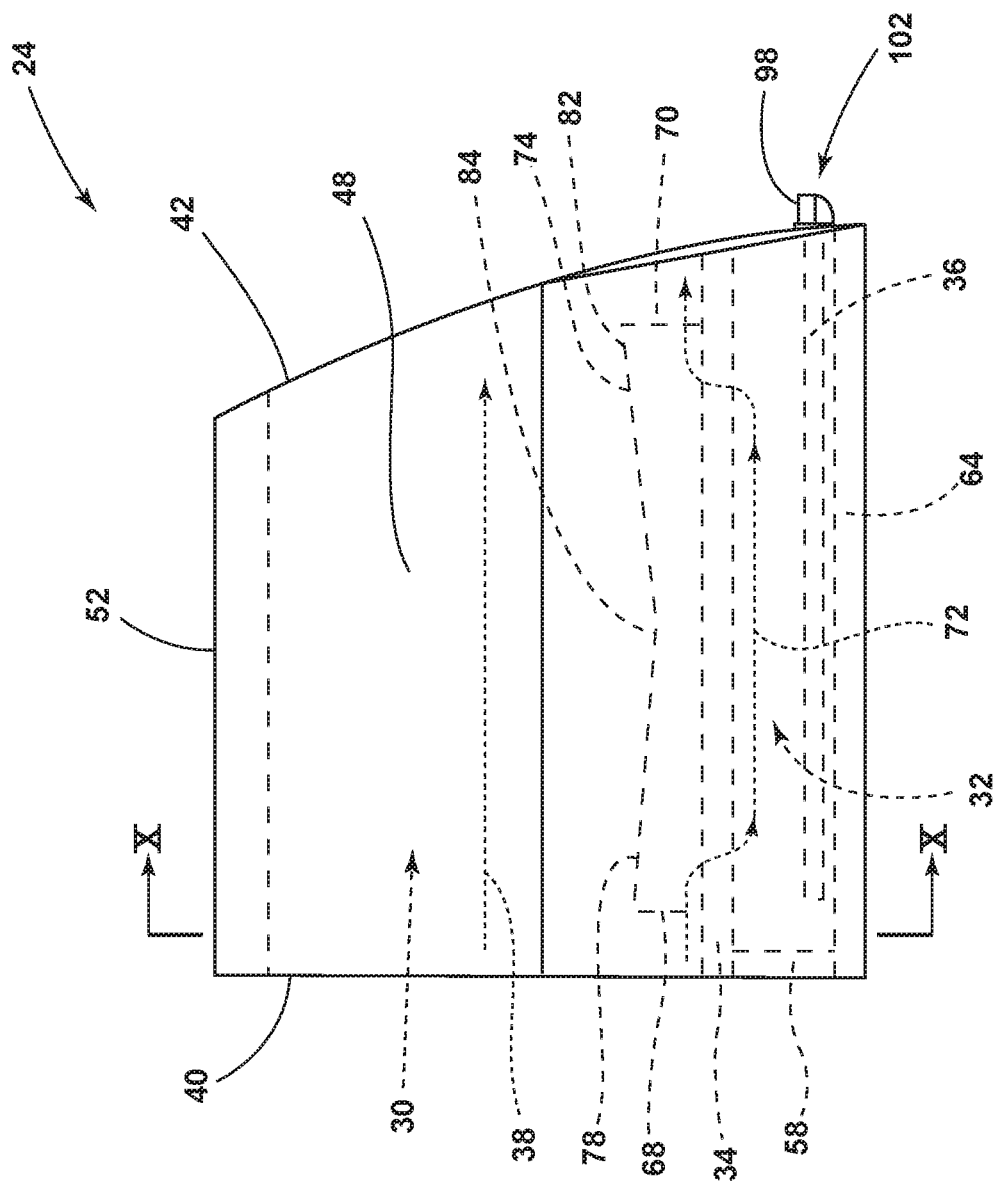
FIG. 7 is a side view of the outlet of FIG. 1, illustrating air diverted from a primary air flow path through the entrance aperture in the dividing wall to take a secondary air flow path through the secondary air flow chamber and out of the secondary air flow chamber through the exit aperture in the dividing wall.
Figure 8:
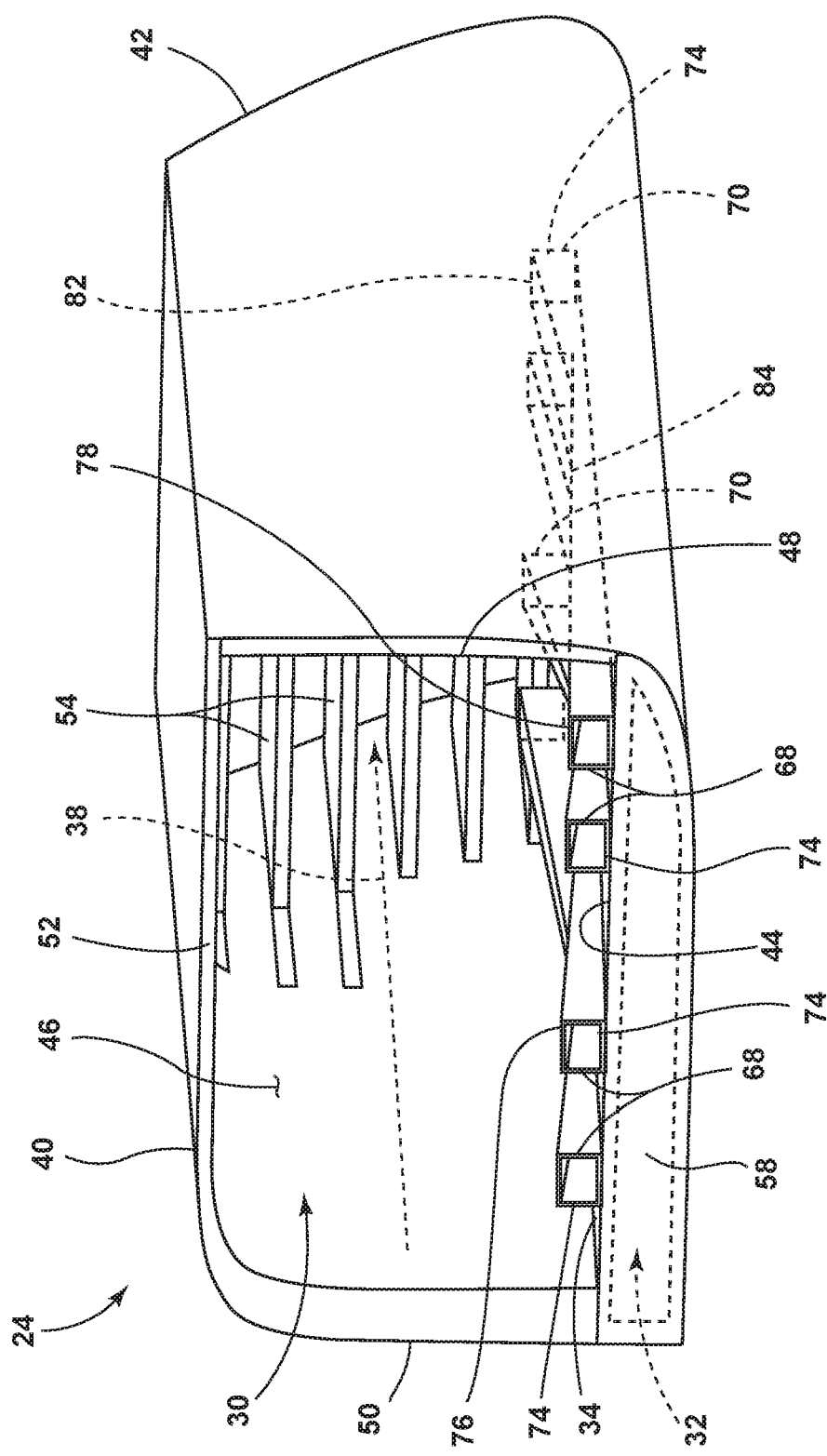
FIG. 8 is a rear perspective view of the outlet of FIG. 1, illustrating the secondary air flow chamber having a rear wall.
Figure 9:
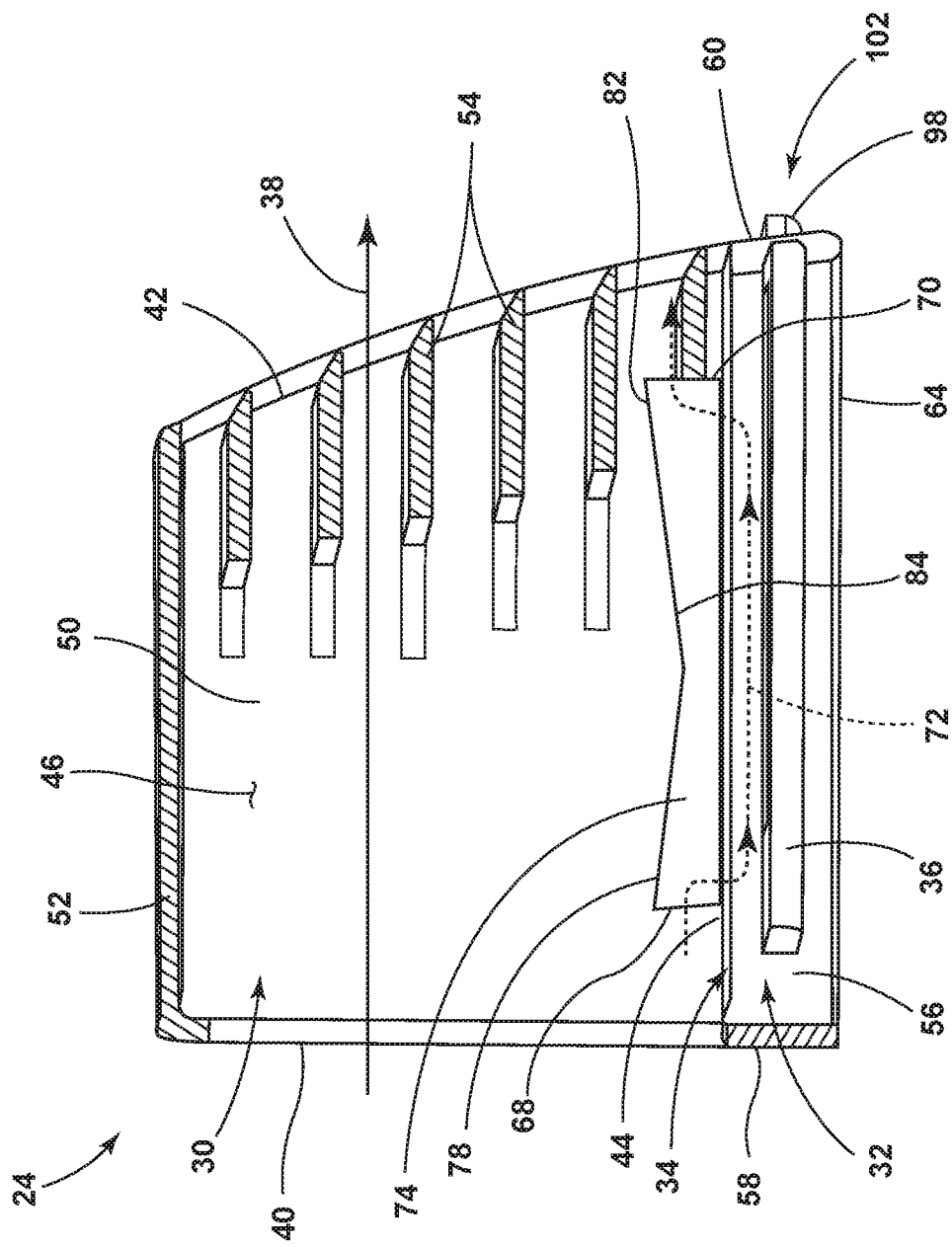
FIG. 9 is a cross-sectional side view of the outlet of FIG. 1 taken through line IX-IX of FIG. 4, illustrating the tray in the full insertion position within the secondary air flow chamber with air flowing in the secondary air flow path over the tray.
Figure 10:
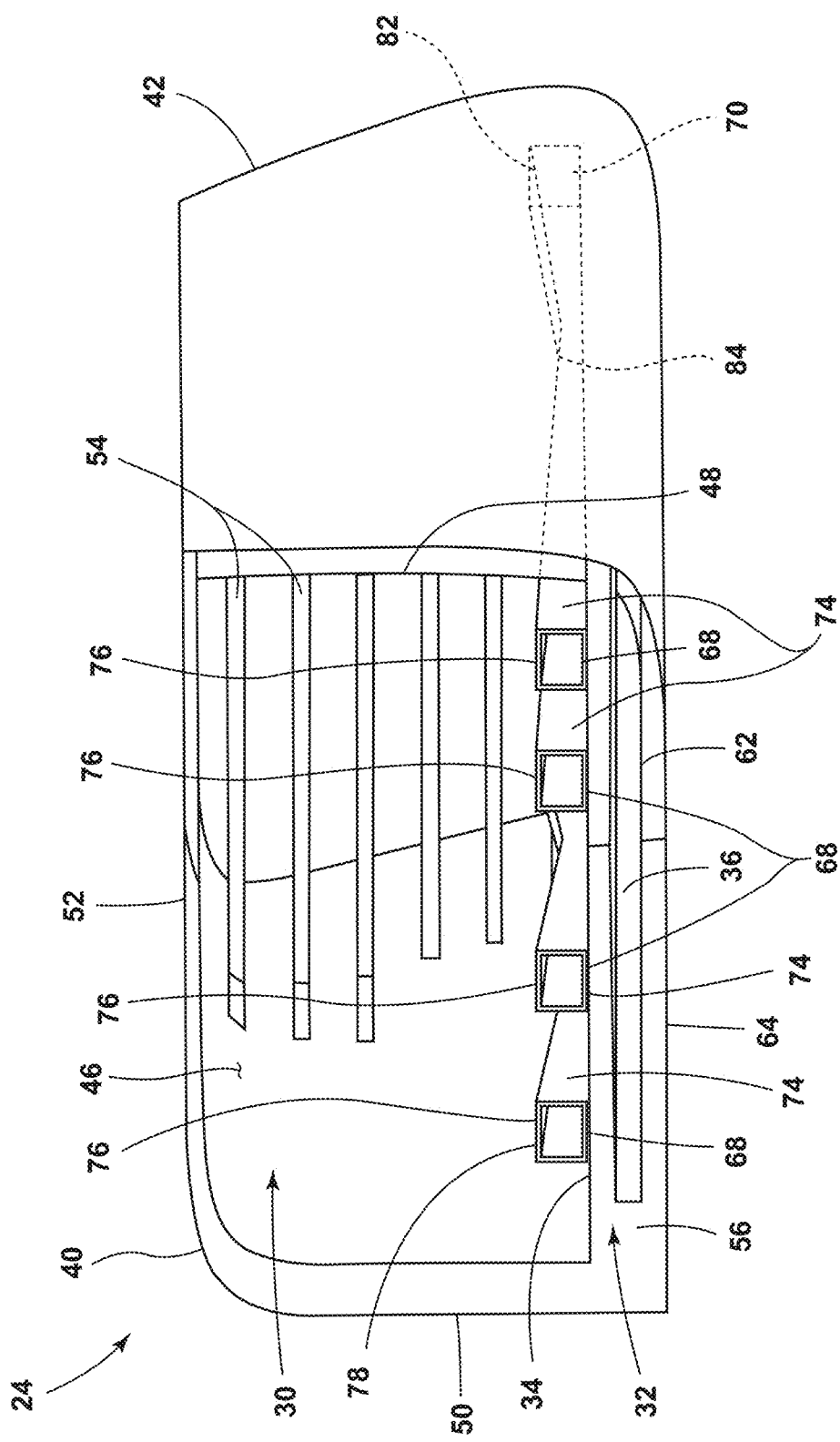
FIG. 10 is a cross-sectional perspective view of the outlet of FIG. 1 taken through line X-X of FIG. 7, illustrating the air flow diverters each having a first edge at a first portion near the entrance of the primary air flow chamber, the first edge defining the entrance aperture into the secondary air flow chamber.
Figure 11:
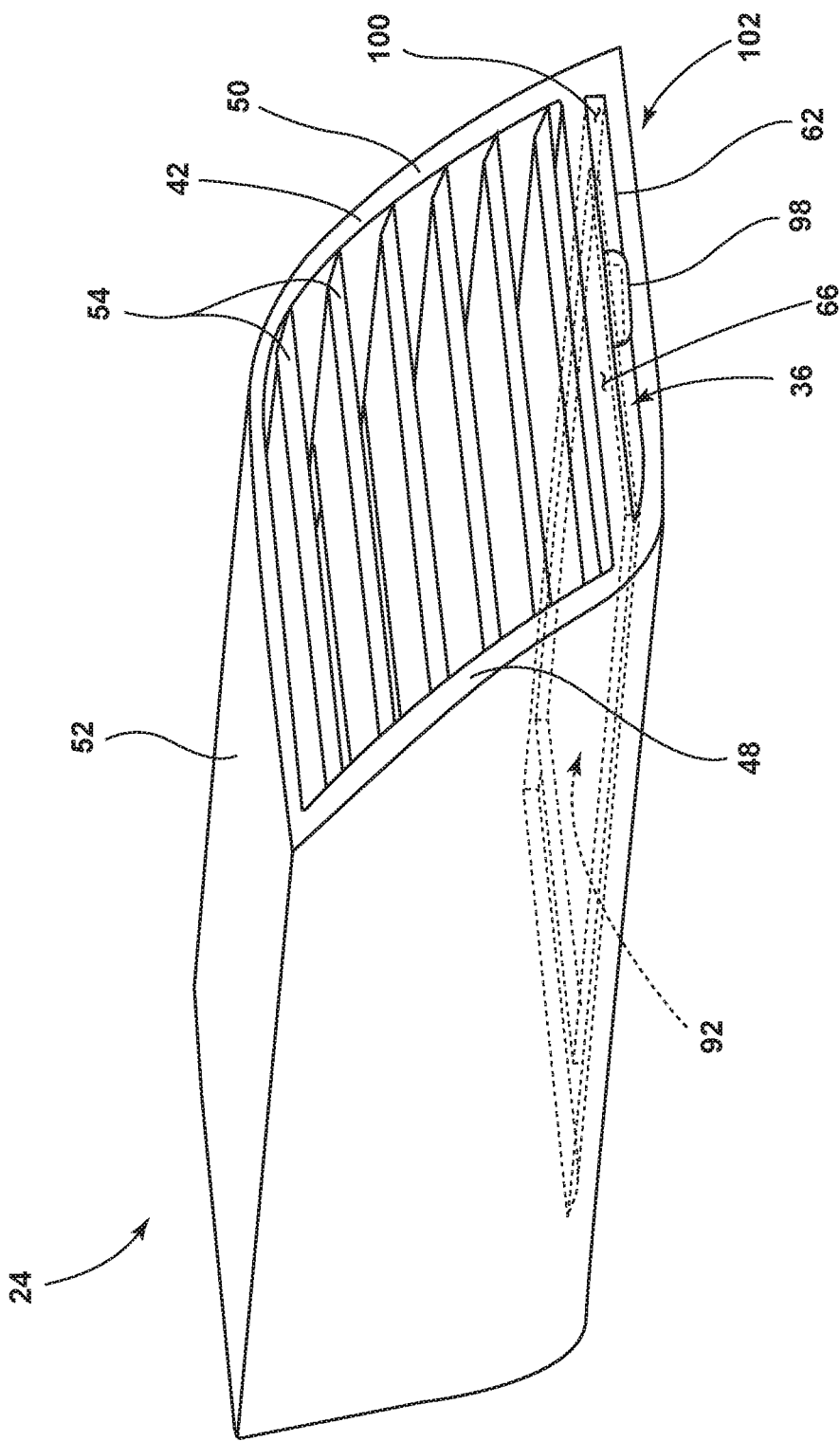
FIG. 11 is a perspective view of the outlet of FIG. 1, illustrating the tray in phantom taking the full insertion position within the secondary air flow chamber.

For purposes of description herein, the terms "forward" and "rear," and derivatives thereof, shall relate to the invention as oriented in FIG. 3, unless the context dictates otherwise. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
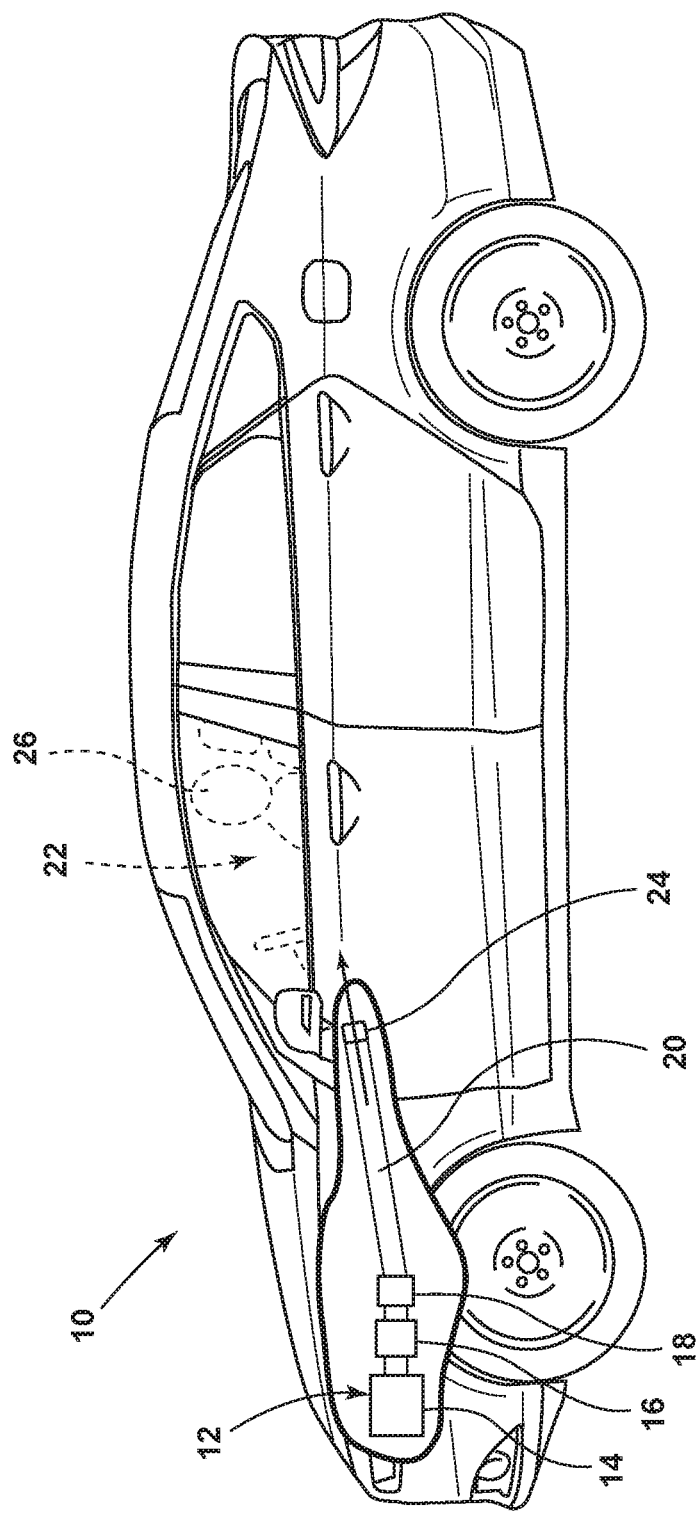
FIG. 1 is a side view of a vehicle, illustrating a forced air system blowing air through an outlet to an interior.
Figure 2:
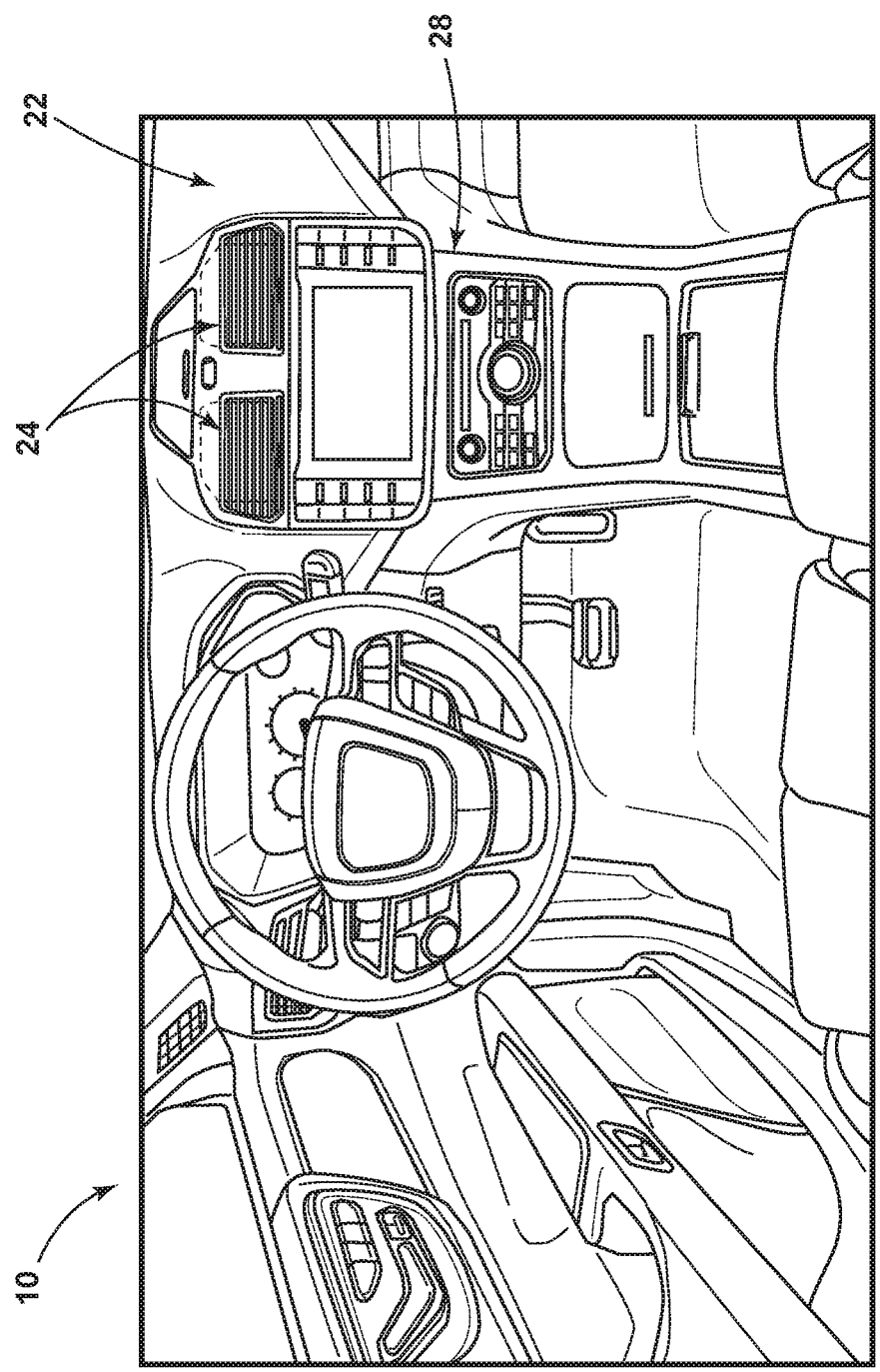
FIG. 2 is a perspective view of the interior of the vehicle of FIG. 1, illustrating the outlet disposed at a center console.

Referring to FIGS. 1 and 2, a vehicle 10 includes a forced air system 12 as is known in the art. The forced air system 12 typically includes a blower 14, a heating element 16, a cooling element 18, and ductwork 20. The forced air system 12 illustrated is highly simplified but sufficient for present purposes. The vehicle 10 further includes an interior 22. The ductwork 20 is in fluid communication with the interior 22. In other words, the forced air system 12, via the blower 14, forces air to flow into the interior 22 via the ductwork 20. The air can be heated by the heating element 16, or cooled by the cooling element 18, or neither. The vehicle 10 further includes an outlet 24. Air that the forced air system 12 forces flows through the outlet 24 before flowing into the interior 22. In use, a person 26 occupies the interior 22 and the vehicle 10 transports the person 26 from one location to another location. In the illustrated embodiment, the vehicle 10 includes a center console 28 and the outlet 24 is disposed at the center console 28. However, the outlet 24 can be disposed elsewhere.

Referring now to FIGS. 3-13 and 15, the outlet 24 includes a primary air flow chamber 30, a secondary air flow chamber 32 that is adjacent the primary air flow chamber 30, a dividing wall 34 separating the secondary air flow chamber 32 from the primary air flow chamber 30, and a tray 36. The primary air flow chamber 30 defines a primary air flow path 38 that extends from the ductwork 20, through an entrance 40 of the outlet 24, and through an exit 42 of the outlet 24 and into the interior 22. The exit 42 is closer to the interior 22 than the entrance 40. The entrance 40 is in fluid communication with and may be physically connected to the ductwork 20 of the forced air system 12. The dividing wall 34 bounds a portion of the primary air flow chamber 30. More specifically, a first surface 44 of the dividing wall 34 and a surface 46 of the primary air flow chamber 30 define the primary air flow chamber 30. In the illustrated embodiment, the primary air flow chamber 30 includes, and is further bound by, opposing side walls 48, 50, and a wall 52 that opposes the dividing wall 34. The surface 46 is contiguously provided by the opposing side walls 48, 50 and the wall 52. The primary air flow chamber 30 can take configurations that are different than the illustrated embodiments. The outlet 24 can further include slats 54, which may be rotatable, to direct the air flow exiting the outlet 24.

The dividing wall 34 additionally bounds a portion of the secondary air flow chamber 32. In the illustrated embodiment, the secondary air flow chamber 32 includes at least one side wall 56, a rear wall 58, a forward wall 60 with an aperture 62, and a wall 64 that opposes the dividing wall 34 and also curves to join the dividing wall 34. The aperture 62 is an inlet through which the tray 36 extends and can move. The forward wall 60 has an interior facing surface 66 that faces the interior 22. The secondary air flow chamber 32 can of course take other configurations. The wall 64 that opposes the dividing wall 34 is, in this embodiment, at least approximately parallel to the wall 52 of the primary air flow chamber 30 that opposes the dividing wall 34.

The dividing wall 34 has at least one entrance aperture 68 and at least one exit aperture 70 as in the illustrated embodiment. Because the dividing wall 34 otherwise separates the primary air flow chamber 30 from the secondary air flow chamber 32, the entrance apertures 68 and exit apertures 70 place the secondary air flow chamber 32 in fluid communication with the primary air flow chamber 30. The entrance apertures 68 are disposed closer to the entrance 40 of the primary air flow chamber 30 than the exit apertures 70. The exit apertures 70 are disposed closer to the interior 22 than the entrance apertures 68. The entrance apertures 68 and the exit apertures 70 allow a portion of the air in the primary air flow path 38 to flow in a secondary air flow path 72. The secondary air flow path 72 is the flow of air in sequence from the primary air flow chamber 30, into one of the entrance apertures 68 through the dividing wall 34, into the secondary air flow chamber 32, out of one of the exit apertures 70 through the dividing wall 34, and back into the primary air flow chamber 30. Except for the aperture 62 through the forward wall 60 and apertures 68, 70 through the dividing wall 34, the secondary air flow chamber 32 is essentially closed off.

In some embodiments of the outlet 24, like the illustrated embodiment, the dividing wall 34 of the outlet 24 further includes at least one air flow diverter 74 that projects into the primary air flow chamber 30. That is, the at least one air flow diverter 74 projects toward the wall 52 of the primary air flow chamber 30 that opposes the dividing wall 34. The air flow diverter 74 is thus between the primary air flow chamber 30 and the secondary air flow chamber 32. The air flow diverters 74 help divert a portion of air flow from the primary air flow chamber 30 to the secondary air flow chamber 32. Each air flow diverter 74 has a first edge 76 at a first portion 78 that includes and defines the entrance aperture 68. As in the illustrated embodiment, the air flow diverter 74 can have a second edge 80 at a second portion 82 that includes and defines the exit aperture 70. The air flow diverter 74, at the first edge 76, places the entrance aperture 68 through the dividing wall 34 at an angle other than parallel (at least an approximately orthogonal angle in the illustrated embodiment) relative to the primary air flow path 38. Thus, air flowing in the primary air flow path 38 will more readily flow through the entrance aperture 68 and into the secondary air flow chamber 32. The exit aperture 70 need not be placed at such an angle relative to the primary air flow path 38 but can be, with the second edge 80 being at least approximately orthogonal to the primary air flow path 38. As in the illustrated embodiment, the air flow diverter 74 can project into the primary air flow chamber 30 to the greatest extent at the first portion 78, and include a middle portion 84 that forces the air flowing through the secondary air flow path 72 further into secondary air flow chamber 32 (and closer to the tray 36, which can retain an aromatic agent as discussed below). More specifically, from the perspective of the secondary air flow chamber 32, the air flow diverter 74 includes a surface 86. The surface 86 extends from the entrance aperture 68 to the exit aperture 70 and faces the tray 36 when the tray 36 is in a full insertion position, as explained below. The surface 86 slopes closer to the tray 36 (and to the wall 64 opposing the dividing wall 34) from the entrance aperture 68 to a closest point 88 and then slopes away from the tray 36 (and the wall 64) from the closest point 88 to the exit aperture 70. The closest point 88 is the point where a distance 89 between the surface 86 and the tray 36 is at a minimum. The surface 86 thus forms a boundary of the secondary air flow path 72 and the secondary air flow chamber 32.

Figure 14:
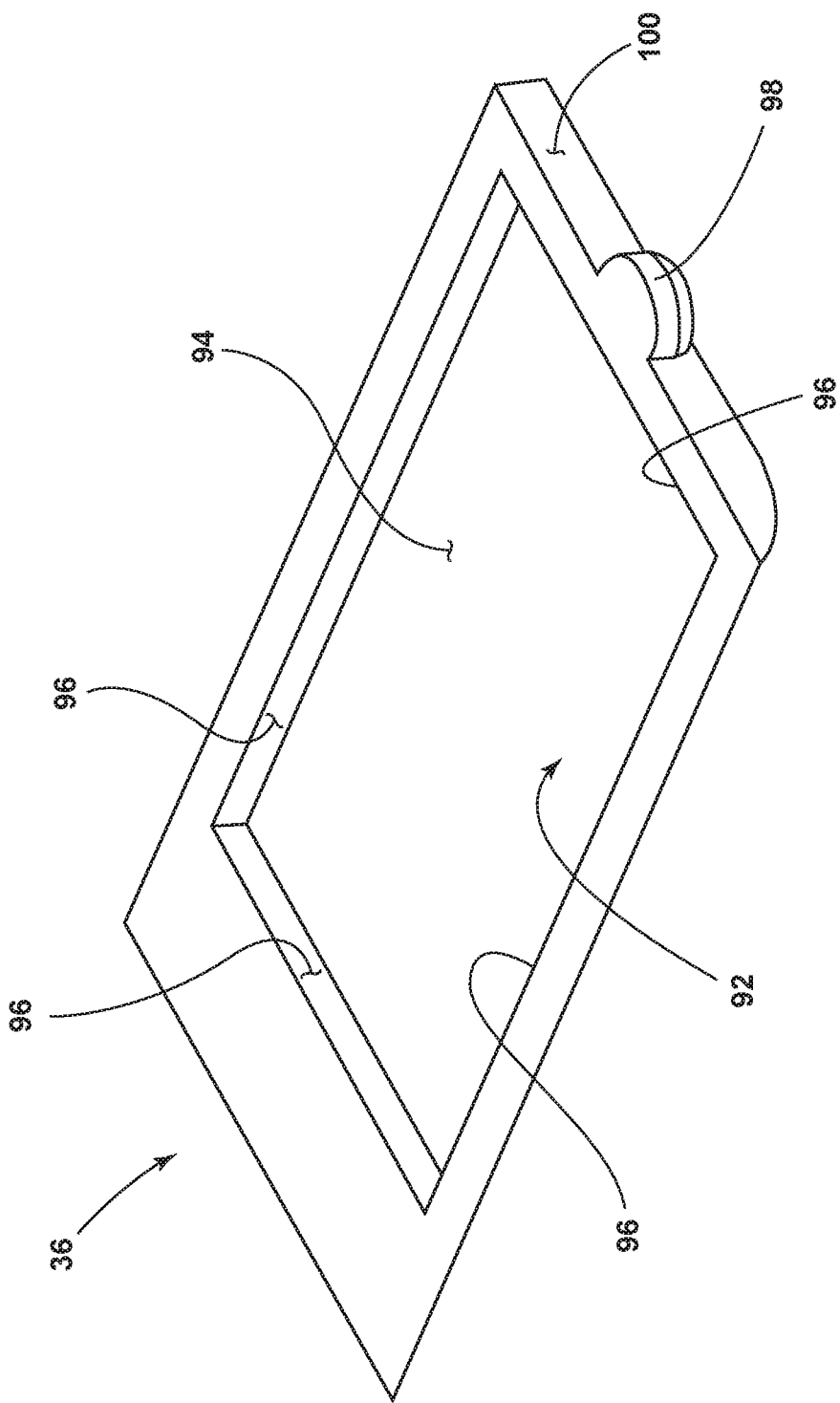
FIG. 14 is an overhead perspective view of the tray of FIG. 11, illustrating a primary reservoir surface and side surfaces extending orthogonally from the primary reservoir surface to the reservoir.
Figure 15:
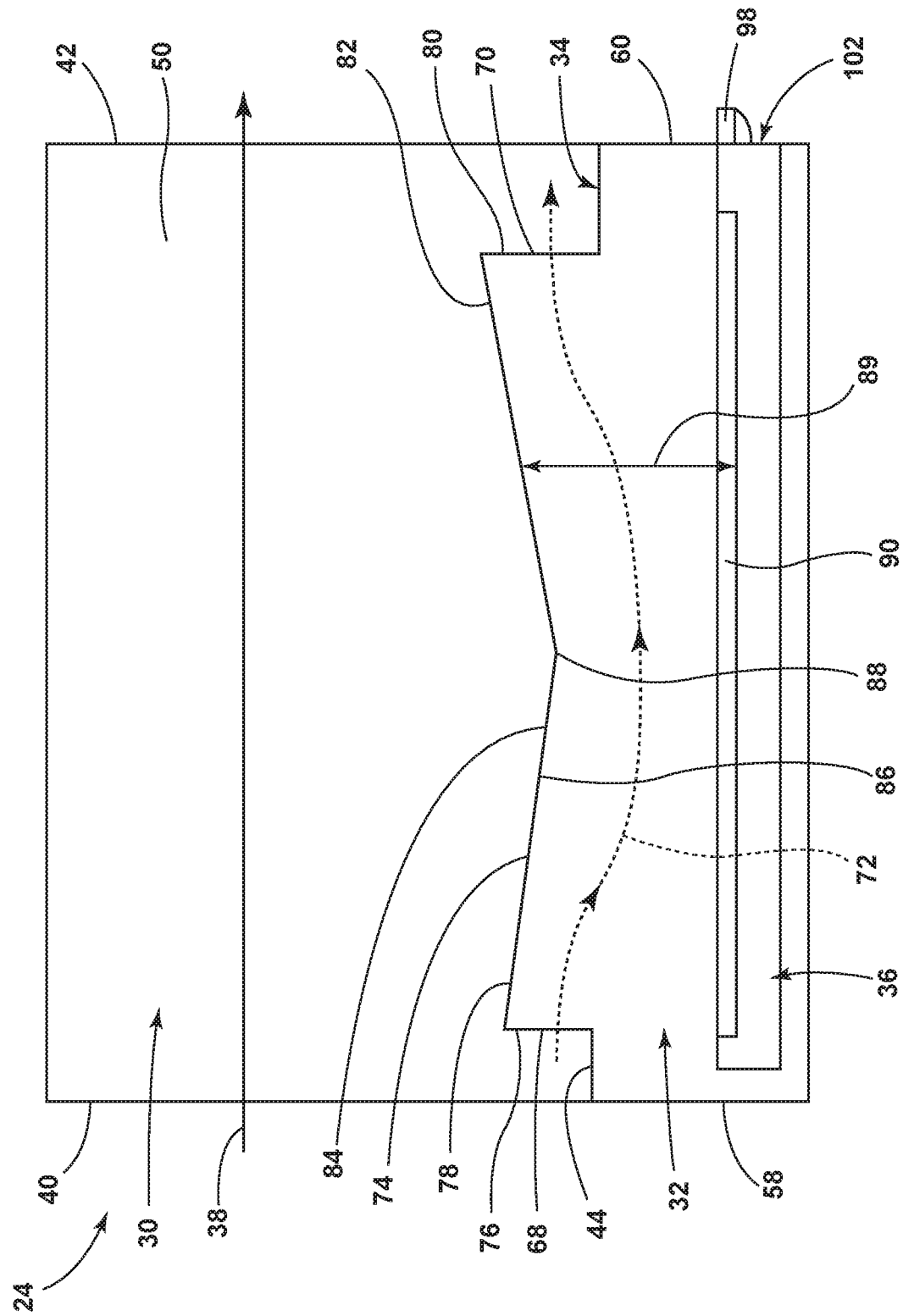
FIG. 15 is a cross-sectional side view of the outlet of FIG. 1 taken along line XV-XV of FIG. 4, illustrating a surface of one of the air flow diverters forcing the secondary air flow path to a closest point to the aromatic agent that the tray holds within the secondary air flow chamber to aromatize air flowing in the secondary air flow path before leaving via the exit aperture to rejoin the primary air flow path and exit the outlet into the interior of the vehicle.

As mentioned, referring additionally to FIG. 14, the outlet 24 further includes the tray 36. The tray 36 is configured to retain an aromatic agent 90. More specifically, the tray 36 includes a reservoir 92. The reservoir 92 can receive and hold the aromatic agent 90. Examples of the aromatic agent 90 include LITTLE TREES® brand of air fresheners that are shaped like trees and come in a variety of scents. More specifically, the reservoir 92 includes a primary reservoir surface 94. The tray 36 further includes one or more side surfaces 96 extending orthogonally from the primary reservoir surface 94 to define the reservoir 92. In the illustrated embodiment, the primary reservoir surface 94 is at least approximately parallel to the dividing wall 34 and to the wall 64 of the secondary air flow chamber 32 that opposes the dividing wall 34. The aromatic agent 90 sits adjacent to (such as over) the primary reservoir surface 94, with the side surfaces 96 helping to hold the aromatic agent 90 in place as the tray 36 is manipulated to different positions, as explained below. The tray 36 further includes a pull tab 98. The pull tab 98 extends away from the reservoir 92, from the outlet 24 generally, and into the interior 22. The pull tab 98 is accessible externally from the outlet 24, that is, from the interior 22, and thus available for the person 26 to manipulate even when the tray 36 is in the full insertion position (further explained below). The tray 36 has an interior facing surface 100, from which the pull tab 98 extends. In the illustrated embodiment, the interior facing surface 100 of the tray 36 and the interior facing surface 66 of the forward wall 60 of the secondary air flow chamber 32 are at least approximately flush when the tray 36 is in the full insertion position (further explained below).

Figure 12:
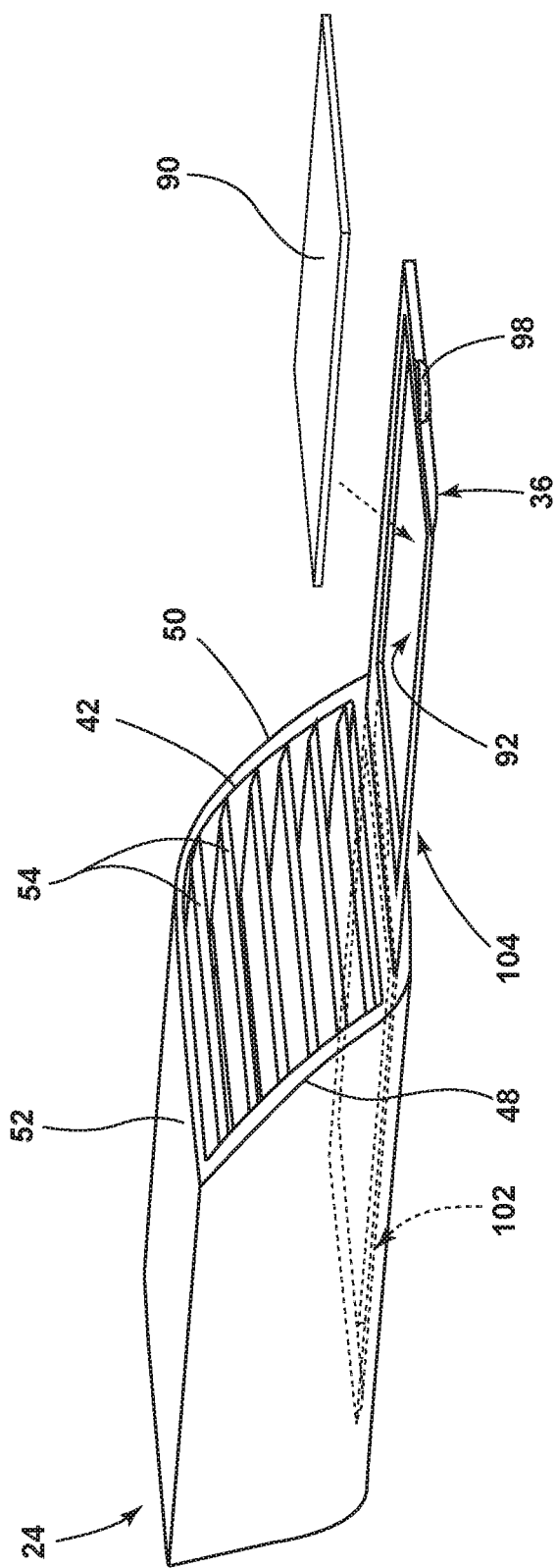
FIG. 12 is a perspective view of the outlet of FIG. 1, illustrating the tray in a loading position extending out of the secondary air flow chamber to expose a reservoir to hold an aromatic agent.
Figure 13:
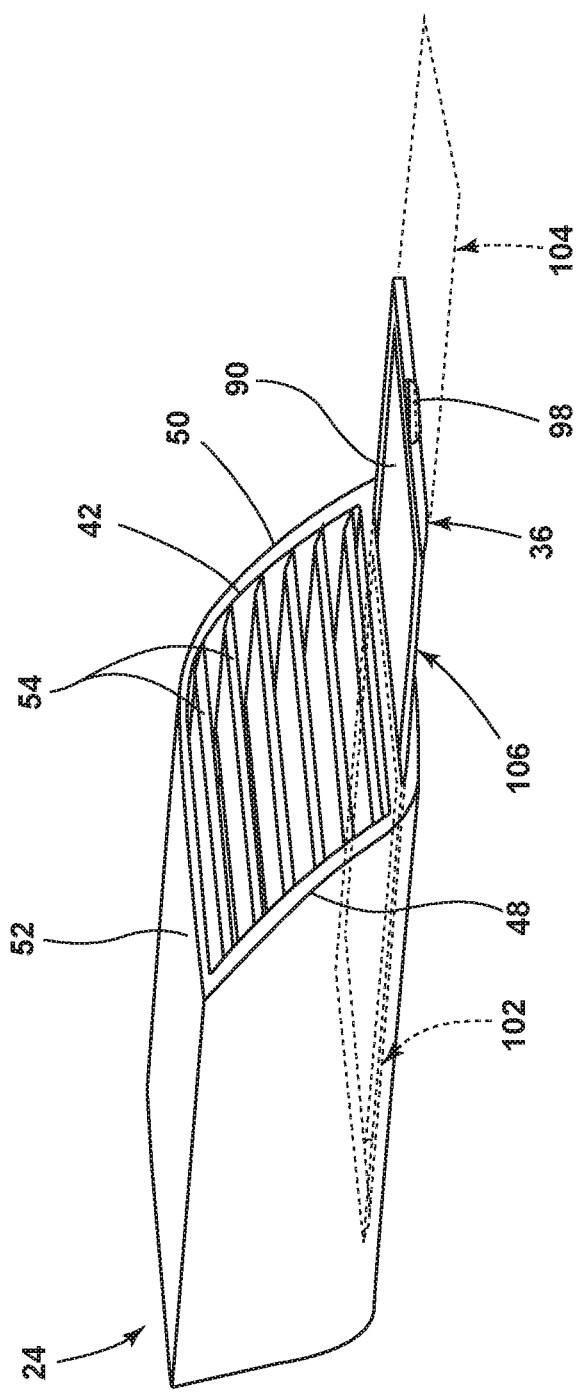
FIG. 13 is a perspective view of the outlet of FIG. 1, illustrating the tray in an intermediate position between the full insertion position (in phantom) and the loading position (in phantom)

As explained further herein, the tray 36 cooperates with the secondary air flow chamber 32. The tray 36 is movable into and out of the secondary air flow chamber 32 to selectively place the aromatic agent 90 in contact with air flowing through the secondary air flow chamber 32 to aromatize the air flowing along the secondary air flow path 72 before flowing back into the primary air flow chamber 30. More specifically, the tray 36 is manipulable to, from, and between a full insertion position 102 (FIGS. 3-11) and a loading position 104 (FIG. 12). In FIG. 13, the tray 36 is illustrated in an intermediate position 106 between the full insertion position 102 and the loading position 104. In the full insertion position 102, the reservoir 92, and any aromatic agent 90 that the reservoir 92 might be holding, is entirely disposed in the secondary air flow chamber 32. In contrast, in the loading position 104, the reservoir 92, and any aromatic agent 90 that the reservoir 92 might be holding, is entirely extracted from the secondary air flow chamber 32. In the loading position 104, the reservoir 92 is disposed sufficiently into the interior 22 to allow for the insertion of the aromatic agent 90 into the reservoir 92. Thus, if the reservoir 92 is not holding any aromatic agent 90 when the tray 36 is in the loading position 104, the reservoir 92 can be loaded with the aromatic agent 90. If the reservoir 92 is holding the aromatic agent 90 when the tray 36 is in the loading position 104, the aromatic agent 90 can be removed from the reservoir 92.

In use, the person 26 pulls on the pull tab 98 to manipulate the tray 36 from the full insertion position 102 to the loading position 104. The tray 36 slides through the aperture 62 in the forward wall 60 of the secondary air flow chamber 32. The person 26 places the aromatic agent 90 within the reservoir 92 of the tray 36. The person 26 then pushes on the tray 36 to move the tray 36 from the loading position 104 to the full insertion position 102 or the intermediate position 106. The person 26 or the vehicle 10 activates the forced air system 12. The forced air system 12 forces air through the ductwork 20 and into the entrance 40 of the outlet 24. Air flows in the primary air flow path 38 from the entrance 40, through the primary air flow chamber 30, out of the exit 42, and into the interior 22. A portion of that air flow flowing through the entrance 40 and into the primary air flow chamber 30 flows through one of the entrance apertures 68 through the dividing wall 34, along the secondary air flow path 72 within the secondary air flow chamber 32. The surface 86 of the air flow diverters 74, if incorporated, forces the air flow in the secondary air flow chamber 32 to the closest point 88 to the tray 36 and thus the aromatic agent 90 that the tray 36 is holding. While in the secondary air flow chamber 32, the air flows over the aromatic agent 90 held in the reservoir 92 of the tray 36. The aromatic agent 90 imparts aroma to the air. The aromatized air then flows out through one of the exit apertures 70 through the dividing wall 34 to rejoin the primary air flow path 38 and then flows into the interior 22. The diverted portion of the air flow that is diverted into the secondary air flow chamber 32 flows back into the primary air flow chamber 30, rejoins the primary air flow path 38, and then flows into the interior 22. The person 26 can regulate the amount of air that the outlet 24 aromatizes by adjusting the position of the tray 36 to the intermediate position 106 between the full insertion position 102 and the loading position 104. For example, the person 26 can increase the amount of air that the outlet 24 aromatizes by placing the tray 36 closer to the full insertion position 102. In contrast, the person 26 can decrease the amount of air that the outlet 24 aromatizes by placing the tray 36 closer to the loading position 104.

Figure 16:
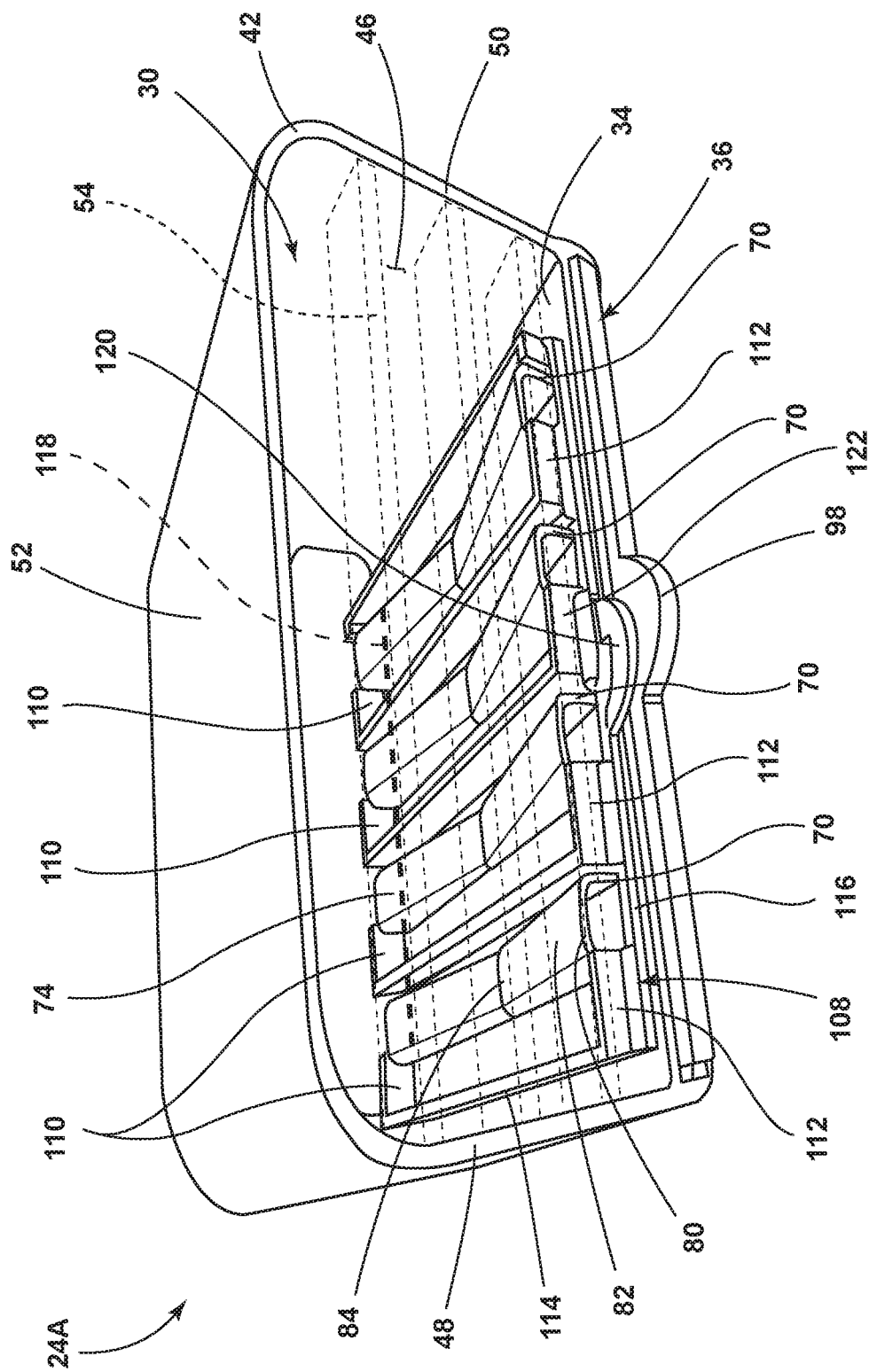
FIG. 16 is a perspective view of an alternative embodiment outlet, illustrating a regulator having entrance flaps to cover the entrance apertures into the secondary air flow chamber, exit flaps to cover the exit apertures out of the secondary air flow chamber, and a tab to selectively position the entrance flaps and exit flaps over the respective entrance apertures and exit apertures.
Figure 17:
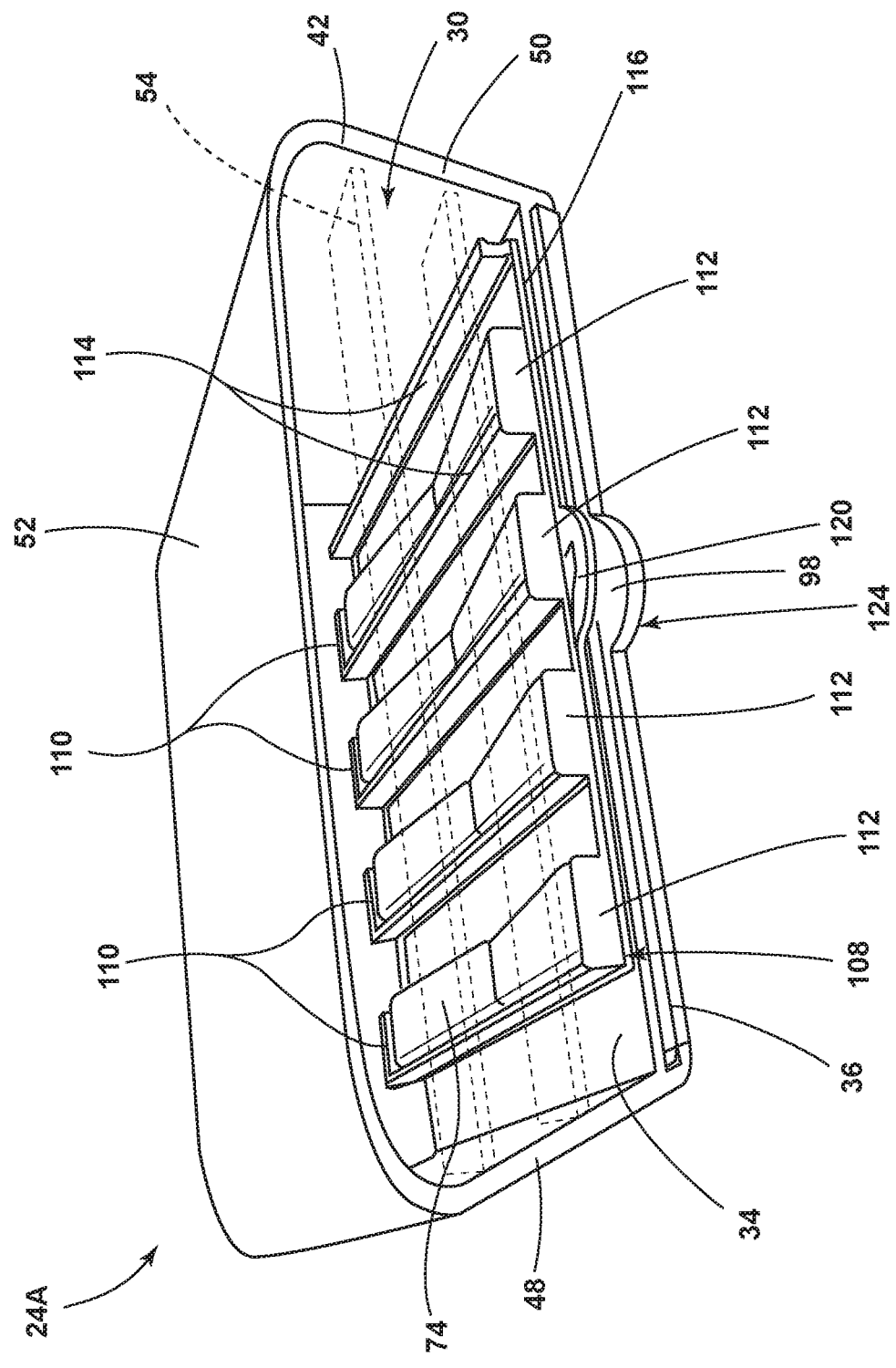
FIG. 17 is a perspective view of the outlet of FIG. 16, illustrating the regulator in a full closed position with the entrance flaps fully covering the entrance apertures into the secondary air flow chamber and the exit flaps fully covering the exit apertures out of the secondary air flow chamber.

Referring now to FIGS. 16 and 17, an alternative embodiment outlet 24A, which is otherwise the same as outlet 24, further includes a regulator 108. The regulator 108 cooperates with the entrance apertures 68 of the dividing wall 34 (and optionally the exit apertures 70) to regulate the volume of air able to flow in the secondary air flow path 72. The regulator 108 includes entrance flaps 110 and optionally exit flaps 112. Each of the entrance flaps 110 are configured to cover one of the entrance apertures 68 of the dividing wall 34. In the illustrated embodiment, because the entrance apertures 68 are orthogonal to the primary air flow path 38, the entrance flaps 110 are orthogonal to the primary air flow path 38 as well. One or more connector portions 114 extending in the direction of the primary air flow path 38 connect pairs of entrance flaps 110 and exit flaps 112 together. An exit lateral connector portion 116 connects the exit flaps 112 together. An entrance lateral connector portion 118 connects the entrance flaps 110 together. The regulator 108 can thus be a single piece. The regulator 108 includes a tab 120. The regulator 108 is manipulable, via the tab 120, to, from, and between a full open position 122 (FIG. 16) and a full closed position 124 (FIG. 17). In the full open position 122, the regulator 108 does not prevent air from the primary air flow path 38 from flowing into the secondary air flow path 72, because the entrance flaps 110 are not covering the entrance apertures 68 into the secondary air flow chamber 32 and the exit flaps 112, if incorporated, are not covering the exit apertures 70 out of the secondary air flow chamber 32. In the full closed position 124, the regulator 108 prevents air from flowing in the secondary air flow path 72, because the entrance flaps 110 are covering the entrance apertures 68 into the secondary air flow chamber 32 and the exit flaps 112, if incorporated, are covering the exit apertures 70 out of the secondary air flow chamber 32. The tab 120 is accessible externally from the outlet 24 (that is, from the interior 22) to allow the person 26 to selectively manipulate the regulator 108 to, from, and between the full open position 122 and the full closed position 124. The person 26 can manipulate the tab 120 to place the regulator 108 between the full closed position 124 and the full open position 122, such that the entrance flaps 110 only partially cover the entrance apertures 68 into the secondary air flow chamber 32 and thus allow only a portion of the primary air flow path 38 be diverted to the secondary air flow path 72 that would otherwise to be diverted if the regulator 108 were in the full closed position 124. The person 26 can thus control the relative volume of air that becomes aromatized via contact with the aromatic agent 90.

In the illustrated embodiments of the outlet 24, 24A, the primary air flow chamber 30 is disposed over the secondary air flow chamber 32 and the tray 36 is held essentially horizontally. However, the primary air flow chamber 30 could be side-by-side with the secondary air flow chamber 32 and the tray 36 held vertically. Likewise, the tray 36 and the secondary air flow chamber 32 could be disposed over the primary air flow chamber 30.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the afore-mentioned structure without departure from the concepts of the present disclosure, and further it is to be understood that such concepts are intended to be covered by the following claims unless these claims by their language expressly state otherwise.

What is claimed is:

1. An outlet for a forced air system of a vehicle comprising:
   a primary air flow chamber defining a primary air flow path from an entrance to an exit;
   a secondary air flow chamber;
   a dividing wall separating the secondary air flow chamber from the primary air flow chamber, the dividing wall comprising entrance apertures into the secondary air flow chamber from the primary air flow chamber and exit apertures out of the secondary air flow chamber into the primary air flow chamber, the entrance apertures being disposed closer to the entrance of the primary air flow chamber than the exit apertures, the entrance apertures and the exit apertures to allow a portion of the air in the primary air flow path to flow in a secondary air flow path in sequence from the primary air flow chamber, into the entrance apertures of the dividing wall, into the secondary air flow chamber, out of the exit apertures through the dividing wall, and back into the primary air flow chamber;
   a tray cooperating with the secondary air flow chamber, the tray including a reservoir to hold an aromatic agent, and the tray manipulable to, from, and between a full insertion position where the reservoir is entirely disposed in the secondary air flow chamber and a loading position where the reservoir is entirely extracted from the secondary air flow chamber; and
   a regulator comprising (i) entrance flaps, (ii) exit flaps, (iii) connector portions extending in the direction of the primary air flow path, each connecting a different one of the entrance flaps to a different one of the exit flaps, (iv) an entrance lateral connector portion that connects the entrance flaps together, and (v) an exit lateral connection portion that connects the exit flaps together, the regulator being manipulatable to, from, and between, (i) a full closed position where the entrance flaps cover the entrance apertures of the dividing wall and the exit flaps cover the exit apertures of the dividing wall and (ii) a full open position where the entrance flaps do not cover the entrance apertures of the dividing wall and the exit flaps do not cover the exit apertures.

2. The outlet of claim 1,
   the primary air flow chamber comprising a wall that opposes the dividing wall; and
   the dividing wall further comprising air flow diverters that project toward the wall of the primary air flow chamber that opposes the dividing wall, each of the air flow diverters comprising a first edge that defines one of the entrance apertures and a second edge that defines one of the exit apertures.

3. The outlet of claim 1,
   the secondary air flow chamber comprising a wall with an apertures through which the tray extends and can move while manipulated to, from, and between the full insertion position and the loading position.

4. The outlet of claim 2,
   each of the air flow diverters, at the first edge thereof, places one of the entrance apertures at an angle other than parallel relative to the primary air flow path.

5. The outlet of claim 2,
   the first edge of each of the air flow diverters and the entrance flaps of the regulator being orthogonal to the primary air flow path.

6. The outlet of claim 2,
   each of the air flow diverters further comprising a surface extending from the entrance aperture to the exit aperture and facing the tray when the tray is in the full insertion position, the surface sloping closer to the tray from the entrance aperture to a closest point, where a distance between the tray and the surface is at a minimum, and then sloping away from the tray from the closest point to the exit aperture.

7. The outlet of claim 1,
   the tray further including a pull tab that extends away from the reservoir and is accessible externally from the outlet when the tray is in the full insertion position.

8. The outlet of claim 1,
   wherein, the regulator further comprises a tab that is accessible externally from the outlet to allow for selective manipulation of the regulator to, from, and between the full open position and the full closed position.

9. The outlet of claim 1,
   the entrance apertures of the dividing wall and the entrance flaps of the regulator are orthogonal to the primary air flow path.

10. A vehicle comprising:
    an interior;
    a forced air system to force air to flow into the interior; and
    an outlet through which air that the forced air system forces flows before flowing into the interior, the outlet comprising:

a primary air flow chamber defining a primary air flow path from an entrance to an exit, the exit being closer to the interior than the entrance;

a secondary air flow chamber;

a dividing wall separating the secondary air flow chamber from the primary air flow chamber, the dividing wall comprising entrance apertures into the secondary air flow chamber from the primary air flow chamber and exit apertures out of the secondary air flow chamber into the primary air flow chamber, the entrance apertures being disposed closer to the entrance of the primary air flow chamber than the exit apertures, the entrance apertures and the exit apertures to allow a portion of the air in the primary air flow path to flow in a secondary air flow path in sequence from the primary air flow chamber, into the entrance apertures of the dividing wall, into the secondary air flow chamber, out of the exit apertures through the dividing wall, and back into the primary air flow chamber;

a tray cooperating with the secondary air flow chamber, the tray including a reservoir to hold an aromatic agent, and the tray manipulable to, from, and between a full insertion position where the reservoir is entirely disposed in the secondary air flow chamber and a loading position where the reservoir is disposed sufficiently into the interior to allow for the insertion of an aromatic agent into the reservoir; and a regulator comprising (i) entrance flaps, (ii) exit flaps, (iii) connector portions extending in the direction of the primary air flow path, each connecting a different one of the entrance flaps to a different one of the exit flaps, (iv) an entrance lateral connector portion that connects the entrance flaps together, and (v) an exit lateral connection portion that connects the exit flaps together, the regulator being manipulatable to, from, and between, (i) a full closed position where the entrance flaps cover the entrance apertures of the dividing wall and the exit flaps cover the exit apertures of the dividing wall and (ii) a full open position where the entrance flaps do not cover the entrance apertures of the dividing wall and the exit flaps do not cover the exit apertures.

11. The vehicle of claim 10, the primary air flow chamber comprising a wall that opposes the dividing wall;

the secondary air flow chamber comprising a wall that opposes the dividing wall; and the dividing wall further comprising air flow diverters that project toward the wall of the primary air flow chamber that opposes the dividing wall, each of the air flow diverters comprising a first edge that defines one of the entrance apertures and a second edge that defines one of the exit apertures.

12. The vehicle of claim 11, each of the air flow diverters, at the first edge thereof, places one of the entrance apertures at an angle other than parallel relative to the primary air flow path.

13. The vehicle of claim 11, the first edge of each of the air flow diverters and the entrance flaps of the regulator being orthogonal to the primary air flow path.

14. The vehicle of claim 11, each of the air flow diverters further comprising a surface extending from the entrance aperture to the exit aperture and facing the tray when the tray is in the full insertion position, the surface sloping closer to the tray from the entrance aperture to a closest point, where a distance between the tray and the surface is at a minimum, and then sloping away from the tray from the closest point to the exit aperture.

15. The vehicle of claim 10, the tray further including a pull tab that extends into the interior, and is available for manipulation, when the tray is in the full insertion position.

16. The vehicle of claim 10, the regulator further comprising a tab that is accessible from the interior to allow for selective manipulation of the regulator to, from, and between the full open position and the full closed position.

17. The vehicle of claim 10 further comprising:

a center console, and the outlet is disposed at the center console.

18. The vehicle of claim 10, the entrance apertures of the dividing wall and the entrance flaps of the regulator are orthogonal to the primary air flow path.

19. The vehicle of claim 10, the secondary air flow chamber having a forward wall with an inlet through which the tray extends and can move, the forward wall having an interior facing surface; and the tray having an interior facing surface, from which a pull tab extends, the interior facing surface of the tray being at least approximately flush with the interior facing surface of the inlet.

20. The vehicle of claim 10, the primary air flow chamber is disposed over the secondary air flow chamber, and the tray is held horizontally within the outlet while the tray is in the full insertion position.

* * * * *